(12) United States Patent
Cherif Cheikh

(10) Patent No.: US 6,896,670 B2
(45) Date of Patent: *May 24, 2005

(54) SAFETY INJECTION DEVICE

(75) Inventor: Roland Cherif Cheikh, Issy les Moulineaux (FR)

(73) Assignee: Societe de Conseils de Recherches et d'Applications Scientifiques, S.A.S., Paris (FR)

( * ) Notice: Subject to any disclaimer, the term of this patent is extended or adjusted under 35 U.S.C. 154(b) by 35 days.

This patent is subject to a terminal disclaimer.

(21) Appl. No.: 10/259,250

(22) Filed: Sep. 26, 2002

(65) Prior Publication Data
US 2003/0114799 A1 Jun. 19, 2003

Related U.S. Application Data

(63) Continuation of application No. 09/400,814, filed on Sep. 22, 1999, now abandoned, which is a continuation of application No. 08/985,693, filed on Dec. 5, 1997, now abandoned, which is a continuation of application No. 08/662,266, filed on Jun. 7, 1996, now Pat. No. 5,695,463, which is a continuation of application No. 08/312,893, filed on Sep. 27, 1994, now abandoned.

(51) Int. Cl.$^7$ ............................................. A61M 31/00
(52) U.S. Cl. ..................................... 604/506; 604/518
(58) Field of Search ............................... 604/57–61, 506, 604/510, 518, 218, 228

(56) References Cited

U.S. PATENT DOCUMENTS

| | | | |
|---|---|---|---|
| 3,016,895 A | 1/1962 | Sein et al. | |
| 3,572,335 A | 1/1969 | Robinson | |
| 3,884,230 A | 5/1975 | Wulff | |
| 4,233,975 A | 11/1980 | Yerman | |
| 4,359,044 A | 11/1982 | Child | |
| 4,774,091 A | 9/1988 | Yamahira et al. | |
| 4,820,267 A | 4/1989 | Harman | |
| 4,834,704 A | 5/1989 | Reinicke | |
| 4,846,793 A | 7/1989 | Leonard et al. | |
| 4,850,968 A | 7/1989 | Romano | |
| 4,994,028 A | 2/1991 | Leonard et al. | |
| 5,098,389 A | 3/1992 | Cappucci | |
| 5,250,026 A | 10/1993 | Ehrlich et al. | |
| 5,275,583 A | 1/1994 | Crainich | |
| 5,279,554 A | 1/1994 | Turley | |
| 5,284,479 A | 2/1994 | de Jong | |
| 5,358,474 A | 10/1994 | Kaldany | |
| 5,433,711 A | 7/1995 | Balaban et al. | |
| 5,437,631 A | 8/1995 | Janzen | |
| 5,487,733 A | 1/1996 | Caizza et al. | |
| 5,501,664 A | 3/1996 | Kaldany | |
| 5,562,613 A | 10/1996 | Kaldany | |
| 5,695,463 A | * 12/1997 | Cherif-Cheikh | 604/60 |
| 6,478,768 B1 | * 11/2002 | Kneer | 604/60 |

FOREIGN PATENT DOCUMENTS

| | | |
|---|---|---|
| EP | 0 292 936 | 11/1988 |
| EP | 0 415 504 | 3/1991 |
| FR | 1 168 371 | 12/1958 |
| NL | 8 901 124 | 12/1990 |
| WO | PCT/IB95/00961 | 6/1996 |

* cited by examiner

*Primary Examiner*—Manuel Mendez
(74) *Attorney, Agent, or Firm*—Fish & Richardson; Brian R. Morrill; Alan F. Feeney

(57) ABSTRACT

An injection device for intramuscular or subcutaneous injection of solid or semi-solid medicaments is disclosed. The device includes main body member having a needle attached thereto. A protective sleeve covers the needle and retracts into the main body member when the device is pressed against the skin of a patient. A plunger with an attached rod maintains the medicament in the patient as the needle is withdrawn.

8 Claims, 3 Drawing Sheets

SAFETY INJECTION DEVICE

CROSS-REFERENCE TO RELATED APPLICATIONS

This application is a continuation (and claims the benefit of priority under 35 USC 120) of U.S. application Ser. No. 09/400,814, filed Sep. 22, 1999, now abandoned which is a continuation of Ser. No. 08/985,693, filed Dec. 5, 1997 (now abandoned), which is a continuation of 08/662,266, filed Jun. 7, 1996 (now U.S. Pat. No. 5,695,463), which is a continuation of Ser. No. 08/312,893, filed Sep. 27, 1994 (now abandoned). The disclosure of the prior applications are considered part of (and are incorporated by reference in) the disclosure of this application.

BACKGROUND OF THE INVENTION

The present invention relates to injection devices and, in particular, to a device for the intramuscular or subcutaneous injection of a pharmaceutically active compound.

The parenteral introduction of pharmaceutically active compounds is preferred over oral dosage in many applications. For example, when the drug to be administered would partially or totally degrade in the gastrointestinal tract, parenteral administration is preferred. Similarly, where there is need for rapid response in emergency cases, parenteral administration is preferred over oral administration.

Thus, while parenteral administration is desirable in many applications, as it is currently practiced it has substantial drawbacks. Probably the biggest drawback is the discomfort which it causes the patient to whom the drug is being administered. Parenteral preparations generally contain a large volume of liquid in which the drug is suspended or dissolved. Ratios of active ingredient to carrier commonly run from 1:100 to 1:1000. When the active ingredient is poorly soluble or difficult to suspend in the carrier, or when the active ingredient has to be administered at high doses, or in both instances, a fairly large volume of liquid must be injected. Both the size of the needle and the volume of liquid being injected cause parenteral administration to be more or less painful, and at least disagreeable, for most people. Furthermore, depending on its nature, the carrier itself may be a cause of pain.

A further disadvantage to administration of drugs in a liquid carrier is that the drugs are frequently not stable in the liquid. Therefore, the liquid and drug must be mixed substantially contemporaneously with injection. This can be of substantial disadvantage where, for example, many hundreds of people must be treated over a course of days in order to stem an epidemic.

Drugs in solid form rather than liquid form have been used for prolonged or controlled release formulations. When the formulation is not a microstructure or a powder that can be injected in suspension form, with a liquid and a standard syringe, the formulation is usually an implant or a rod which can be injected directly via a trocar, see for example European Patent Application Publication No. 0292936. However, trocars and the device as set forth in the cited European Patent have some disadvantages. When the formulation is a prolonged or controlled formulation, the formulation must contain the daily dose of drug multiplied by the number of days of activity of the drug and the amount of carrier necessary to control the rate of delivery of that drug. Thus this formulation, which is in the needle, requires a needle significantly larger than ordinary needles used with syringes and this results in a painful injection.

SUMMARY OF THE INVENTION

The applicant has now discovered a comparatively inexpensive device for the ready administration of solid or substantially solid drugs by the parenteral route wherein the drugs are intended to be immediately assimilated by the body.

Because the quantity of drug is just the amount needed for an immediate effect and because there is no need for carriers to control function, the needle can be as small as ordinary needles. The drug is stable because it is in solid form and, thus, no contemporaneous mixing is needed. The injection is substantially painless because the needle size for the injected volume is dramatically reduced as compared to the size needed for liquid injection. The risk of contamination can be reduced because there is no pre-manipulation of the injectable formulation before making the injection. A seal can be fitted on the tic of the injection member so that there is complete sterility until injection into the skin.

Finally, because there is no volume of liquid to inject, the procedure is simplified.

The applicants herein filed a co-pending application Ser. No. 08/304,274 on Sep. 12, 1994 entitled NEEDLE-LESS PARENTERAL INTRODUCTION DEVICE, the teaching of which is hereby incorporated by reference. The device in this co-pending application comprises a housing and a plunger. The plunger pushes a solid medicament out of a bore in the housing and directly into the patient. This device works very well for drugs which can be made structurally strong enough to penetrate the skin. However, it has been found that there are some drugs which cannot be made structurally strong enough. While such drugs could be combined with a structurally strong carrier, there are instances where the use of a carrier is undesirable.

In accordance with the present invention the applicants have developed a device similar to the NEEDLE-LESS PARENTERAL INTRODUCTION DEVICE except that in the instant case the device includes a needle. Unlike past devices, however, the device of the present invention has a needle which is never exposed to the outside elements. Thus it can never pick up airborne contaminants, nor can it inadvertently scratch someone, such as a hospital worker. This aspect is especially important for treatment of mentally unstable patients.

These and other aspects of the present invention may be more fully understood with respect to the drawings.

Figure 1:
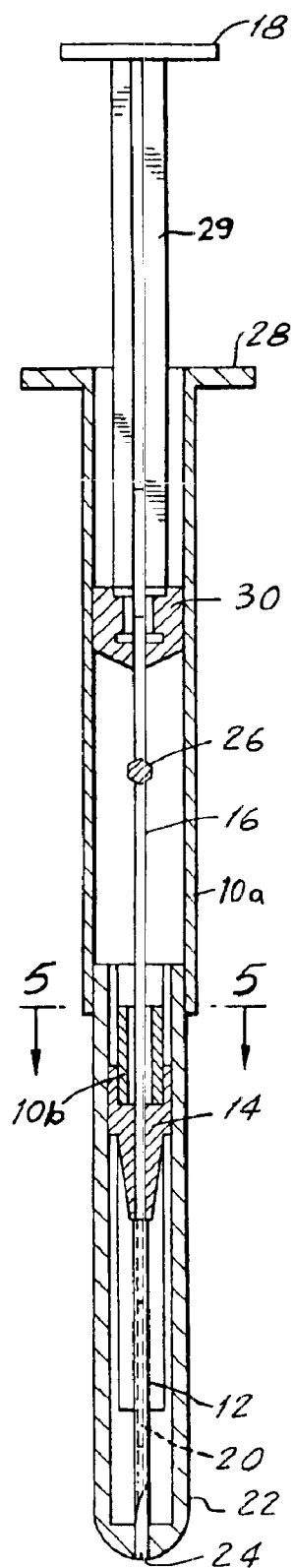
FIG. 1 shows the device at rest.

Referring first to FIG. 1 there is shown main body member 10a, 10b which is attached to needle 12 through coupling means 14. A rod 16 is guided into needle 12 and abuts medicament 20 which is positioned in needle 12. A sleeve 22 surrounds needle 12 so that needle 12 is not exposed until used. Sleeve 22 is provided with one or more slots 40 (see FIG. 5) along its length so that main body members 10a and 10b can be joined by radially extending connecting members 42. A seal 24 covers the opening 23 and the slots 40 of sleeve 22 in order to maintain the sterility of needle 12 and medicament 20. The seal is preferably of easily friable material such as wax. Rod 16 includes a bulb 26 which serves as a stop for travel of the rod 16. Main body member 10 has a flange 28 to assist in removal of the device after injection. Rod 16 is attached to a plunger 29 which has a top thumb flange 18. A guide 30 is attached to plunger 29 and is positioned in main body member 10 to guide plunger 29 and rod 16.

Figure 2:
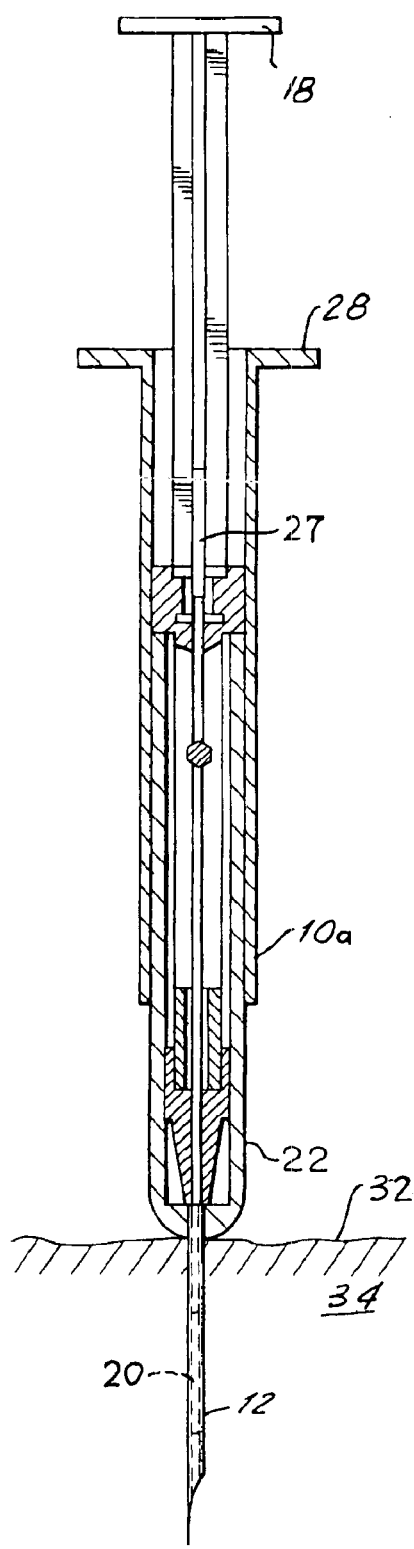
FIG. 2 shows the device with the needle injected into the patient.

FIG. 2 shows the device of FIG. 1 wherein needle 12 has penetrated the skin 32 of the person being treated. As shown, needle 12 has penetrated through the skin 32 into the subcutaneous layer 34. As the device of FIG. 1 is pressed against the skin 32, sleeve 22 is retracted into main body member 10 by the force of pressure against the skin 32.

Figure 3:
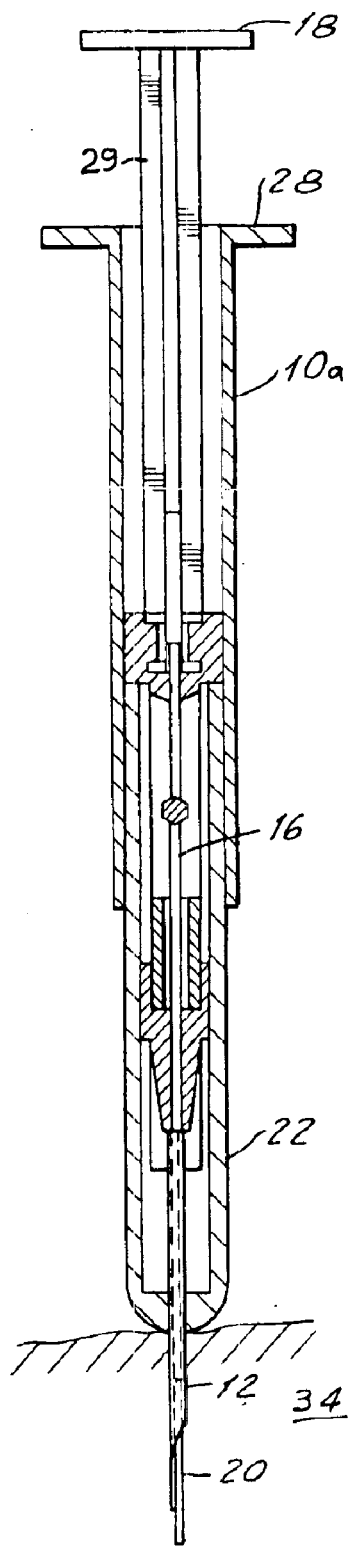
FIG. 3 shows the needle being withdrawn with the medicament remaining in the patient.

At this point, and as shown in FIG. 3, main body member 10 is moved in an upward direction by exerting finger pressure against the lower part of flange 28 while simultaneously exerting opposing pressure with the thumb on flange 18 of plunger 29. This relative movement of the plunger 29 and the main body member 10 causes the needle 12 to retract into sleeve 22 thus leaving medicament 20 in the subcutaneous layer 34 of the patient.

Figure 4:
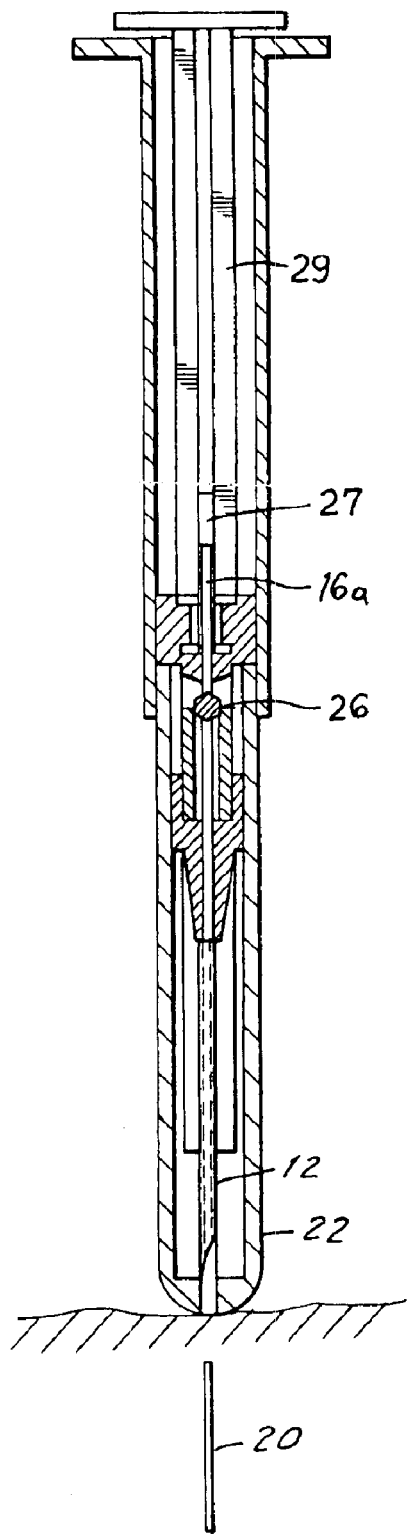
FIG. 4 shows complete withdrawal of the needle from the patient.

FIG. 4 shows the needle 12 fully withdrawn into sleeve 22 and with medicament 20 remaining in the subcutaneous layer 34 of the patient. As can also be seen in FIG. 4, the upper portion 15a of rod 16 has been pushed into a bore 27 in plunger 29 by the action of coupling means 14 against bulb 26 of rod 16.

Figure 5:
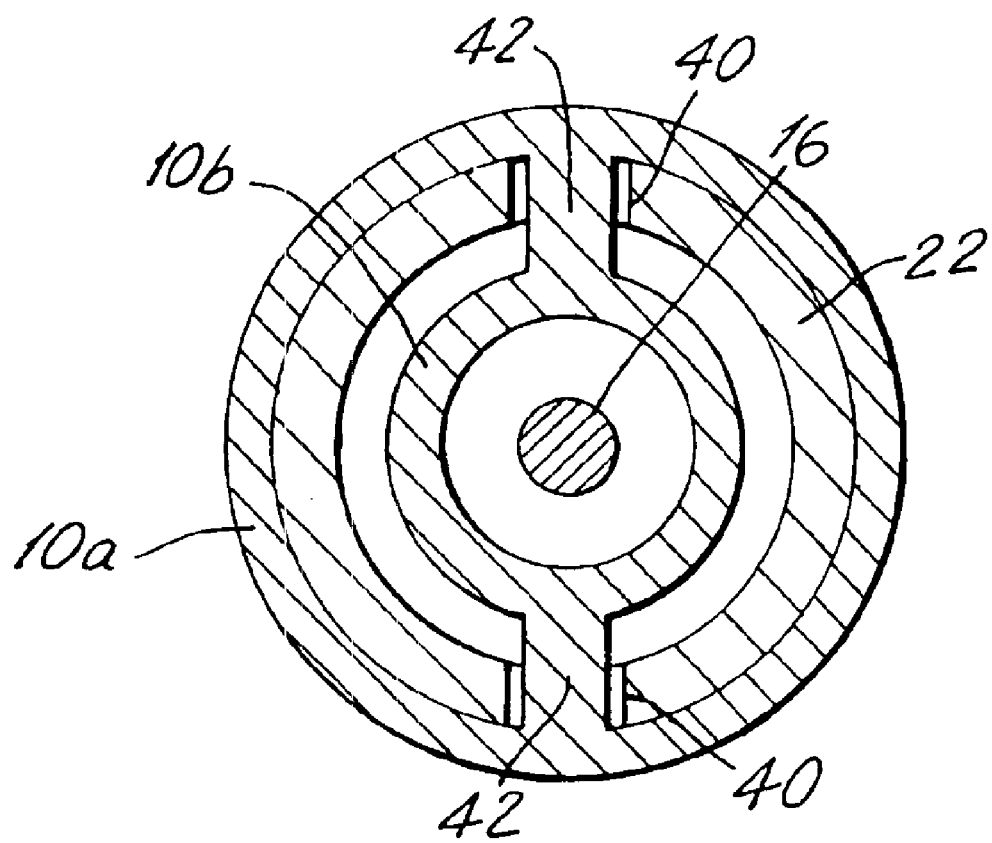
FIG. 5 shows a cross-section through line 5—5 of FIG. 1.

FIG. 5 is a cross-sectional view of FIG. 1 at 5—5. FIG. 5 shows slots 40 in sleeve 22. Radially extending connecting members 42 extend through the slots 40 to join main body member 10a with main body member 10b.

As will be appreciated from the foregoing drawings and description, the only time that the needle came out of its protective sleeve was when it was already abutted against the patient's skin. At no time is the needle ever exposed to the air where it could become contaminated or where it might inadvertently scratch someone.

Turning now to the medicament 20, it is preferred that it be solid or semi-solid. It is preferred that the device of the present invention be used with a medicament that is not strong enough to penetrate the skin; however, in some applications, it is acceptable for the medicament to have such strength. The amount of carrier, if present, should be as small as possible. As a general rule, the amount of active ingredient in the medicament 20 is at least 20% and is preferably above 50%. With suitable medicaments which will hold a shape, the amount of medicament can be up to 100%. The medicament may be prepared by conventional techniques such as compression, thermofusion or extrusion. Compression suitably consists of a tabletting process in which a microtablet is formed. The diameter of the medicament 20 may be up to 2 mm but is preferably from about 0.25 to about 0.5 mm in diameter and about 1 to about 3 cm in length. The diameter of the rod 16 is preferably about the same diameter as the diameter of the medicament 20. The inside diameter of the needle 12 is preferably just slightly larger than the diameter of the medicament. It is preferred that the needle 12 and rod 16 be metallic, notably stainless steel; the balance of the components can be relatively inexpensive plastic materials.

It will be understood that the claims are intended to cover all changes and modifications of the preferred embodiments of the invention herein chosen for the purpose of illustration which do not constitute a departure from the spirit and scope of the invention.

What is claimed is:

1. A method of administering a medicament to a patient, the method comprising:

providing an injection device for injecting a medicament parenterally into a mammal, the device including a main body member, a hollow needle affixed to the main body member, a plunger being slidably positioned in the main body member, a rod within the needle, the rod extending through the main body member and the rod being affixed to the plunger, and a hollow sleeve that covers the needle prior to injection, the sleeve being slidably positioned in the main body member, and wherein when the device is pressed against skin of a mammal the sleeve retracts into the main body member thereby exposing the needle and allowing the needle to penetrate the skin of the mammal, wherein when the plunger is pushed into the main body member, the plunger contacts and forces the sleeve out of the main body member thereby withdrawing the needle from the mammal, and wherein the plunger and rod are operative to push the medicament through the needle into the mammal as the needle is being withdrawn from the mammal;

depressing the device against the skin of the mammal, to thereby allow the sleeve to retract into the main body member and the needle to penetrate the skin of the mammal; and depressing the plunger, thereby forcing the medicament through the skin, to thereby administer the medicament to the mammal.

2. The method of claim 1, wherein the rod includes a bulb which functions as a stop for the rod when the plunger is pushed into the main body member.

3. The method of claim 2, wherein the plunger includes a flange.

4. The method of claim 3, wherein the main body member includes a flange.

5. The method of claim 4, wherein the sleeve includes an opening covered by a seal operative to maintain the sterility of the needle.

6. The method of claim 1, wherein the medicament is semi-solid.

7. The method of claim 1, wherein the medicament is solid.

8. The method of claim 7, wherein the diameter of the medicament is from about 0.25 to about 0.5 mm and the length of the medicament is from about 1 cm to about 3 cm.

* * * * *